US00PP20739P2

(12) United States Plant Patent
van Hees

(10) Patent No.: US PP20,739 P2
(45) Date of Patent: Feb. 9, 2010

(54) POINSETTIA PLANT NAMED 'PER16806'

(50) Latin Name: ***Euphorbia pulcherrima* Willd.**
Varietal Denomination: PER16806

(75) Inventor: Giles van Hees, Forest Hill, MD (US)

(73) Assignee: The Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 12/284,870

(22) Filed: Sep. 22, 2008

(51) Int. Cl.
*A01H 5/00* (2006.01)

(52) U.S. Cl. ..... Plt./303; Plt./306

(58) Field of Classification Search ..... Plt./303, Plt./306
See application file for complete search history.

(56) References Cited

U.S. PATENT DOCUMENTS

PP7,825 P * 3/1992 Fruehwirth ..... Plt./307
PP12,604 P2 * 5/2002 Gross ..... Plt./306
PP19,282 P2 * 10/2008 Kobayashi ..... Plt./306
PP19,504 P2 * 11/2008 von Danwitz ..... Plt./303

OTHER PUBLICATIONS

UPOV ROM GTITM Computer Database, GTI Jouve Retrieval Software 2008/03 Citation for 'PER16806'.*
Gu, Sanjun. Evaluation of New Poinsettia Varieties in Central Missoure, Poster Board # 186. Jul. 25, 2009. ASHS Meeting Millennium Hotel, St. Louis, MO. Available at:http://ashs.confex.com/ashs/2009/webprogram/Paper2780.html.*

* cited by examiner

*Primary Examiner*—Wendy C Haas
(74) *Attorney, Agent, or Firm*—C. A. Whealy

(57) ABSTRACT

A new and distinct cultivar of Poinsettia plant named 'PER16806', characterized by its uniform, upright, outwardly spreading and mounded plant habit; moderately vigorous growth habit; freely branching habit; dark green-colored leaves; early season flowering response; inflorescences with pink-colored flower bracts with dark pink-colored speckles; and good post-production longevity.

1 Drawing Sheet

Botanical designation: *Euphorbia pulcherrima* Willd.
Cultivar denomination: 'PER16806'.

BACKGROUND OF THE INVENTION

The present invention relates to a new and distinct cultivar of Poinsettia plant, botanically known as *Euphorbia pulcherrima* Willd., and hereinafter referred to by the name 'PER16806'.

The new Poinsettia plant is a naturally-occurring whole plant mutation of *Euphorbia pulcherrima* Willd. '490', disclosed in U.S. Plant Pat. No. 7,825. The new Poinsettia was discovered and selected by the Inventor as a single plant from within a population of plants '490' in a controlled greenhouse environment in Forest Hills, Md. in November, 2005.

Asexual reproduction of the new Poinsettia plant by terminal vegetative cuttings in a controlled greenhouse environment in Forest Hills, Md. since January, 2006, has shown that the unique features of this new Poinsettia plant are stable and reproduced true to type in successive generations of asexual reproduction.

SUMMARY OF THE INVENTION

Plants of the new Poinsettia have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'PER16806'. These characteristics in combination distinguish 'PER16806' as a new and distinct cultivar of Poinsettia:

1. Uniform, upright, outwardly spreading and mounded plant habit.
2. Moderately vigorous growth habit.
3. Freely branching habit.
4. Dark green-colored leaves.
5. Early season flowering response; under natural season conditions, plants flower in about 7.5 weeks in Encinitas, Calif.
6. Inflorescences with light pink-colored flower bracts covered with dark pink-colored speckles.
7. Good post-production longevity.

In side-by-side comparisons conducted in Encinitas, Calif., plants of the new Poinsettia differed from plants of the parent, '490', primarily in flower bract color as plants of '490' have dark red-colored flower bracts.

Plants of the new Poinsettia can be compared to plants of the *Euphorbia pulcherrima* Willd. 'Amazone', disclosed in U.S. Plant Pat. No. 12,604. In side-by-side comparisons conducted in Encinitas, Calif., plants of the new Poinsettia differed from plants of 'Amazone' in the following characteristics:

1. Plants of the new Poinsettia had darker green-colored leaves than plants of 'Amazone'.
2. Plants of the new Poinsettia flowered earlier than plants of 'Amazone' under natural season conditions.

BRIEF DESCRIPTION OF THE PHOTOGRAPHS

The accompanying photographs illustrate the overall appearance of the new Poinsettia. These photographs show the colors as true as it is reasonably possible to obtain in colored reproductions of this type. Colors in the photographs may differ slightly from the color values cited in the detailed botanical description which accurately describe the colors of the new Poinsettia.

The photograph at the bottom of the sheet comprises a side perspective view of a typical flowering plant of 'PER16806' grown in a container.

The photograph at the top of the sheet is a close-up view of typical inflorescences of 'PER16806'.

DETAILED BOTANICAL DESCRIPTION

Plants used in the aforementioned photographs and the following observations and measurements describe plants grown in Encinitas, Calif. during the autumn and winter in a polyethylene-covered greenhouse and under conditions and practices which approximate those generally used in commercial Poinsettia production. During the production of the plants, day temperatures averaged 24° C., night averaged 19° C. and light levels were about 4,000 foot-candles. Measurements and numerical values represent averages for typical flowering plants. Single plants were grown in 15.25-cm pots and pinched one time. Plants had been growing for 17 weeks when the photographs and the description were taken. In the following description, color references are made to The Royal Horticultural Society Colour Chart, 1995 Edition, except where general terms of ordinary dictionary significance are used.

Botanical classification: *Euphorbia pulcherrima* Willd. 'PER16806'.

Parentage: Naturally-occurring whole plant mutation of the *Euphorbia pulcherrima* Willd. '490', disclosed in U.S. Plant Pat. No. 7,825.

Propagation:

*Type.*—Termimal vegetative cuttings.

*Time to initiate roots.*—About five to seven days at 21° C.

*Time to produce a rooted young plant.*—About four weeks at 21° C.

*Root description.*—Fibrous; white in color.

Plant description:

*Plant habit and form.*—Uniform, upright, outwardly spreading and mounded plant habit; inverted triangle. Inflorescences positioned above the foliar plane. Vigorous growth habit.

*Plant height.*—About 30 cm.

*Plant diameter or spread.*—About 48 cm.

*Lateral branch description.*—Quantity: Freely branching habit, about seven lateral branches develop after pinching. Length: About 24 cm. Diameter: About 6 mm. Internode length: About 1.5 cm. Strength: Strong. Texture: Smooth, glabrous. Color: Close to 146B.

*Foliage description.*—Arrangement: Alternate, simple. Length: About 11.8 cm. Width: About 8 cm. Shape: Ovate with occasional shallow lobes. Apex: Acuminate. Base: Acute. Margin: Entire; occasional shallow lobes. Venation pattern: Pinnate, arcuate. Texture, upper and lower surfaces: Pubescent. Color: Developing leaves, upper surface: Close to 147A. Developing leaves, lower surface: Close to 147B. Fully expanded leaves, upper surface: Close to 139A; venation, close to 147C. Fully expanded leaves, lower surface: Darker than 147B; venation, close to 147C. Petiole: Length: About 5.3 cm. Diameter: About 3 mm. Texture, upper and lower surfaces: Smooth, glabrous. Color, upper surface: Close to 146C. Color, lower surface: Close to 146D.

Inflorescence description:

*Inflorescence type and habit.*—Inflorescences are compound corymbs of cyathia with colored flower bracts subtending the cyathia; inflorescences positioned above the foliage.

*Quantity of inflorescence.*—One inflorescence develops per lateral branch.

*Fragrance.*—Not detected.

*Natural flowering season.*—Plants typically flower during the autumn and winter in Encinitas, Calif. Inflorescence initiation and development can also be induced under artificial long nyctoperiod/short photoperiod conditions. Early season flowering habit, plants flower about 7.5 weeks under natural season conditions in Encinitas, Calif.

*Post-production longevity.*—Good post-production longevity; plants of the new Poinsettia maintain good substance and bract color for about four weeks under interior conditions; inflorescences persistent.

*Inflorescence size.*—Diameter: About 34 cm. Height (depth): About 7 cm.

*Flower bracts.*—Quantity per inflorescence: About 20. Length, largest bracts: About 16.2 cm. Width, largest bracts: About 12.3 cm. Shape: Ovate. Apex: Acuminate. Base: Acute. Margin: Entire; occasional shallow lobes. Texture, upper and lower surfaces: Smooth, glabrous. Aspect: Close to perpendicular to the stem axis; bending back with development. Venation pattern: Pinnate, arcuate. Color: Developing or transitional bracts, upper surface: Close to 11C tinted with close to 50C; venation, close to 146D. Developing or transitional bracts, lower surface: Close to 50C to 50D; venation, close to 147D. Fully expanded bracts, upper surface: Close to 50B; speckles, close to 50A; venation, close to 12D. Ground color becoming closer to 50C with development. Fully expanded bracts, lower surface: Close to 38D; venation, close to 145B to 145C. Bract petiole: Length: About 3.8 cm. Diameter: About 2.5 mm. Texture, upper and lower surfaces: Smooth, glabrous. Color, upper and lower surfaces: Close to 145B.

*Cyathia.*—Quantity per corymb: About eight. Diameter of cyathia cluster: About 2.5 cm by 2.8 cm. Length: About 1.2 cm. Width: About 5 mm. Shape: Ovoid. Color, immature: Close to 145A. Color, mature: Close to 144A. Nectaries: Quantity per cyathium: One. Size: About 2 mm by 3 mm. Color: Close to 2A.

*Peduncles.*—Length: About 3 mm. Diameter: About 2 mm. Strength: Strong. Aspect: Mostly upright. Texture: Smooth, glabrous. Color: Close to 144B.

*Reproductive organs.*—Stamens: Quantity per cyathium: About 15 to 18. Filament length: About 3 mm. Filament color: Close to 2D. Anther shape: Oval; bi-lobed. Anther length: About 1 mm. Anther color: Close to 9A. Amount of pollen: Moderate. Pollen color: Close to 9A. Pistils: Plants of the new Poinsettia do not develop pistils. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15° C. to about 30° C.

It is claimed:

1. A new and distinct Poinsettia plant named 'PER16806' as illustrated and described.

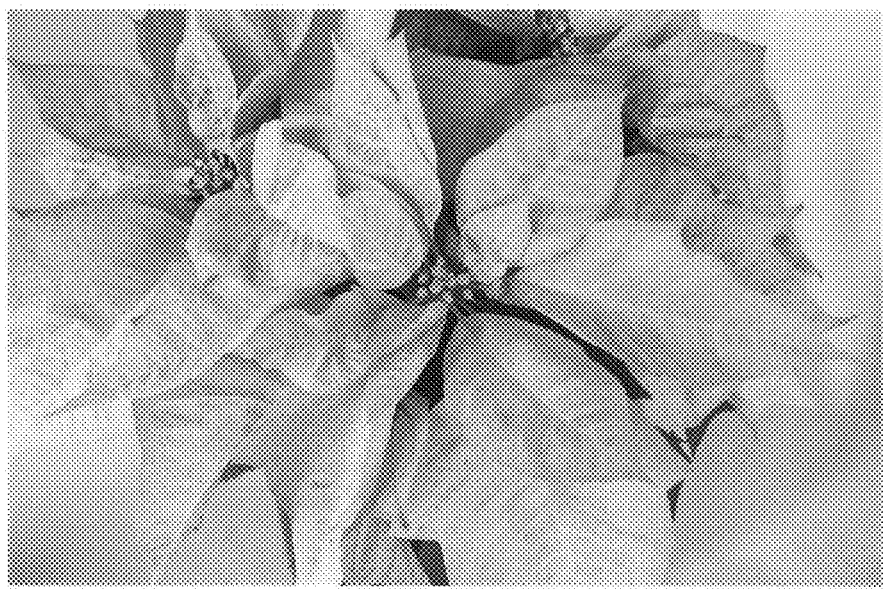
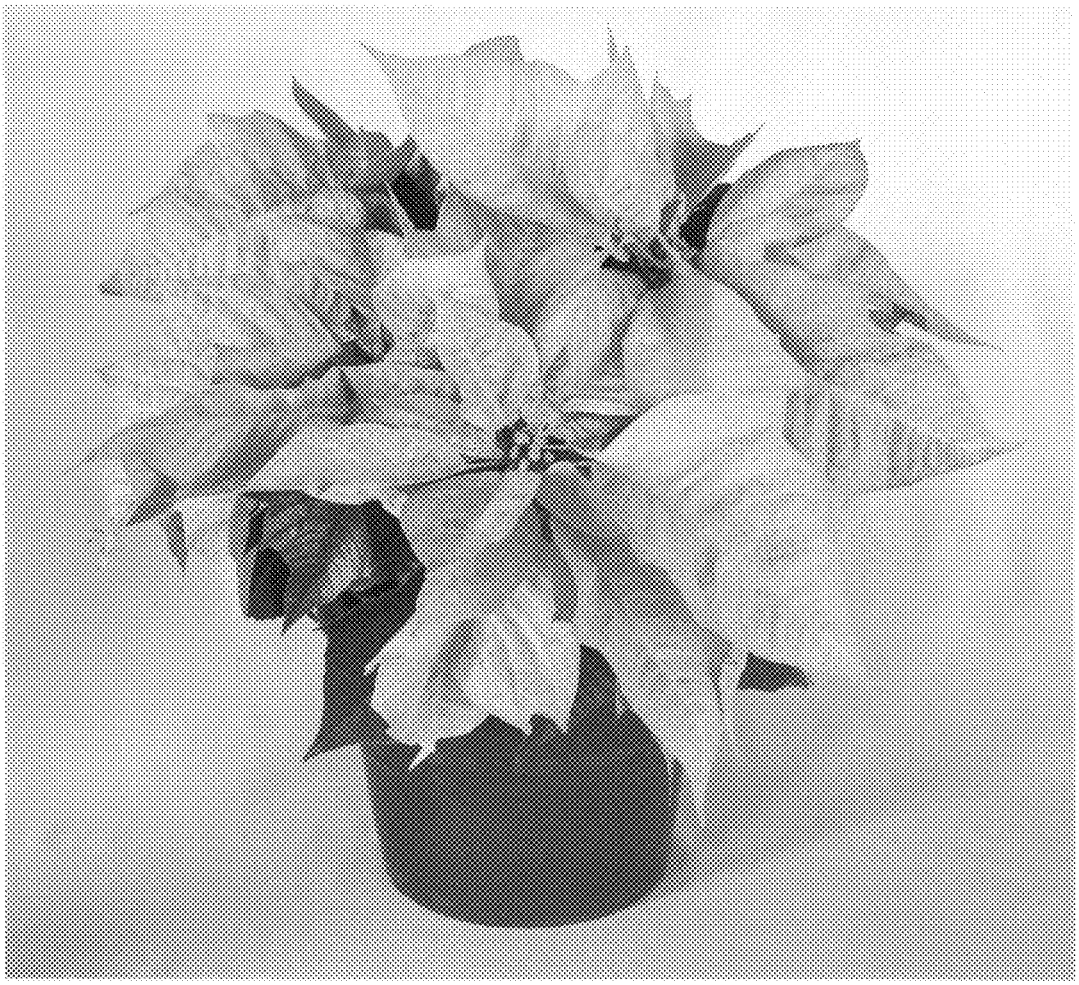

* * * * *